United States Patent [19]

Belanger et al.

[11] 4,271,474
[45] Jun. 2, 1981

[54] APPARATUS FOR DETECTING AND MEASURING THE HYDROGEN CONTENT IN A LIQUID SUBSTANCE

[75] Inventors: Guy Belanger; Gilles Missout, both of St-Bruno, Canada

[73] Assignee: Hydro-Quebec, Quebec, Canada

[21] Appl. No.: 963,518

[22] Filed: Nov. 24, 1978

[30] Foreign Application Priority Data

Sep. 18, 1978 [CA] Canada .................................. 311484

[51] Int. Cl.³ .......................................... G01N 27/46
[52] U.S. Cl. ............................... 364/500; 204/195 P; 364/104; 422/81
[58] Field of Search ............... 204/1 T, 195 P, 195 R; 364/497, 500, 104; 324/29, 464; 422/81

[56] References Cited

U.S. PATENT DOCUMENTS

| | | | |
|---|---|---|---|
| 3,325,378 | 6/1967 | Greene et al. ........................ | 204/1 T |
| 3,509,034 | 4/1970 | Paine ................................. | 204/195 P |
| 3,654,113 | 4/1972 | ................................... | Bochinski/204 |
| 3,672,843 | 6/1972 | Rosse et al. ..................... | 204/195 P X |
| 3,874,850 | 4/1975 | Sorensen et al. .................... | 422/81 X |
| 3,963,440 | 6/1976 | Stein et al. ..................... | 204/195 P X |
| 3,997,420 | 12/1976 | Buzza ............................. | 204/195 P |
| 4,039,933 | 8/1977 | Moran ............................ | 324/29 |
| 4,090,848 | 5/1978 | Naono ............................ | 422/81 |
| 4,121,907 | 10/1978 | Roque ........................... | 422/81 X |
| 4,127,111 | 11/1978 | Drolet ........................... | 422/81 X |

OTHER PUBLICATIONS

G. Belanger et al., IEEE Trans. Electr. Insul. vol. EI-12, No. 5, pp. 334-340, (1977).
Kent Tech. Rev., No. 15, pp. 17-19, Feb. 1976.

Primary Examiner—G. L. Kaplan
Attorney, Agent, or Firm—Schwartz, Jeffery, Schwaab, Mack, Blumenthal & Koch

[57] ABSTRACT

The invention relates to an apparatus for measuring the concentration of gaseous hydrogen dissolved in a liquid substance. The apparatus comprises an electrochemical cell constituted of a polymeric membrane in contact with a sample of the liquid substance and which is permeable to hydrogen, of an electrolyte capable of causing an oxidation reaction of the hydrogen diffused through the polymeric membrane, at a first electrode, and a reduction reaction of an oxygenated gas at a second electrode, so as to deliver an electric current proportional to the hydrogen concentration to be measured. An electrovalve operates, when activated, to exhaust the liquid substance sample at a predetermined instant in the measuring process. Moreover, the circuit amplifies a voltage corresponding to the value of the current proportional to the concentration, which current flows through a load resistance mounted in parallel across the first and second electrodes and the input of the amplifying circuit. A display device is connected to the output of the amplifying circuit and supplies a digital measure of the hydrogen concentration in the liquid substance. A control unit determines the operation times of the electrochemical cell, of the electrovalve as well as of the digital display device pursuant to a predetermined sequence.

16 Claims, 14 Drawing Figures

APPARATUS FOR DETECTING AND MEASURING THE HYDROGEN CONTENT IN A LIQUID SUBSTANCE

BACKGROUND OF THE INVENTION

The present invention concerns an apparatus for detecting and measuring the concentration of the hydrogen gas dissolved in a liquid substance, and more particularly relates to an apparatus able to detect and measure the hydrogen content of a liquid according to an automatic operation process and following a preestablished sequence.

Presently, there exist several systems capable of detecting the concentration of the hydrogen gas dissolved in liquids, but those systems call for a constant attention from the operator since the latter has to intervene at various stages of the measuring process in order to gather valid results. That requirement rapidly becomes wearisome for the operator, is rather costly and often gives rise to errors in the interpretation of the results.

SUMMARY OF THE INVENTION

The present invention is directed to an apparatus which avoids the above inconveniences and advocates a relatively low-cost apparatus which is able to govern in an automatic manner the various steps of a measuring process without requiring any operator's intervention.

More specifically, the present invention is relative to an apparatus for detecting and measuring the concentration of hydrogen gas dissolved in a liquid substance, which comprises an electrochemical detection device operative to determine the concentration of hydrogen gas in a sample of the liquid substance and to generate a current of a value proportional to that concentration; a device, connected to the detection device, for draining the liquid sample therefrom; a display device for displaying the concentration detected by the detection device; and a control circuit for controlling operation times of the detection device, the draining device and display device pursuant to a predetermined process sequence.

BRIEF DESCRIPTION OF THE DRAWINGS

Preferred embodiments of the present invention will be hereinafter described with reference to the accompanying drawings, wherein.

DETAILED DESCRIPTION OF PREFERRED EMBODIMENTS

Figure 1:
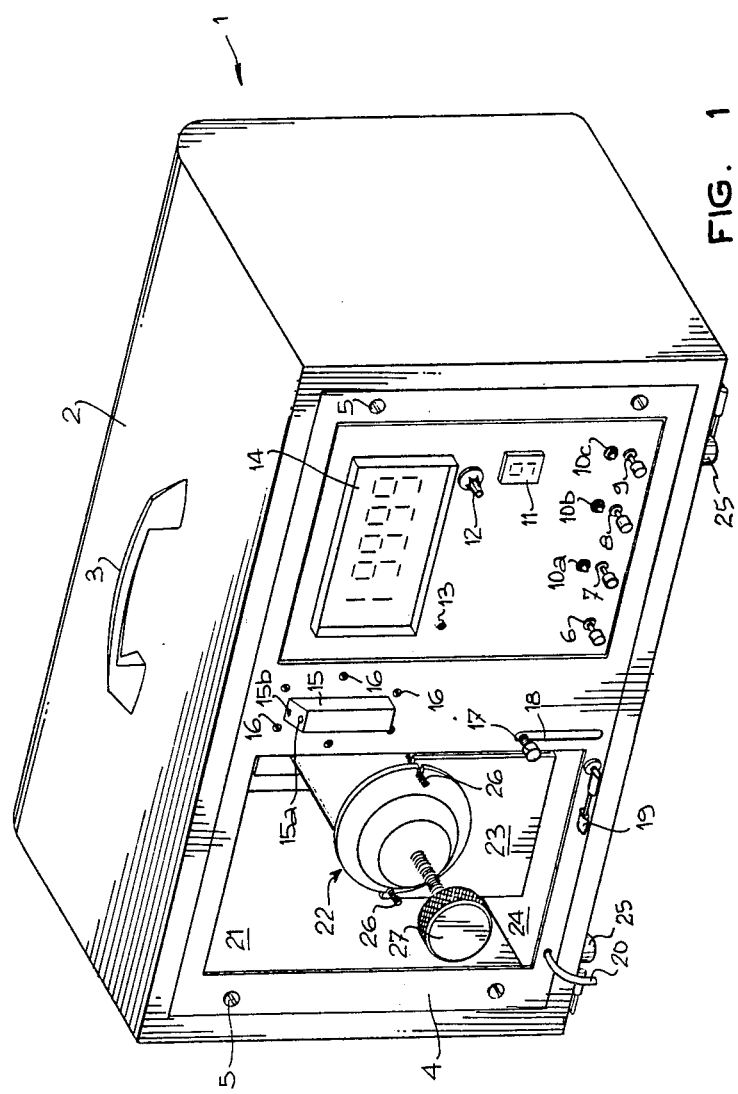
FIG. 1 is a perspective view of the apparatus for measuring the concentration of a hydrogen gas in a liquid, according to the present invention.
Figure 2:
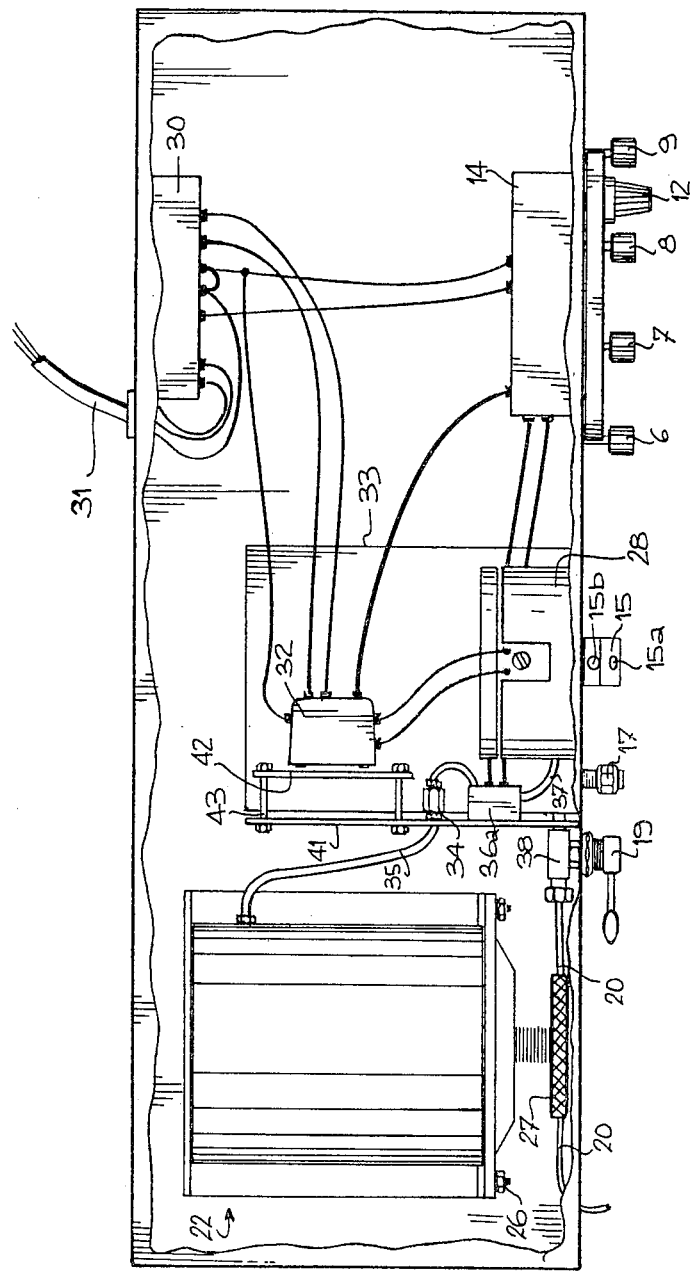
FIG. 2 is a top view showing the physical arrangement of the devices inside the measuring apparatus of FIG. 1.
Figure 3:
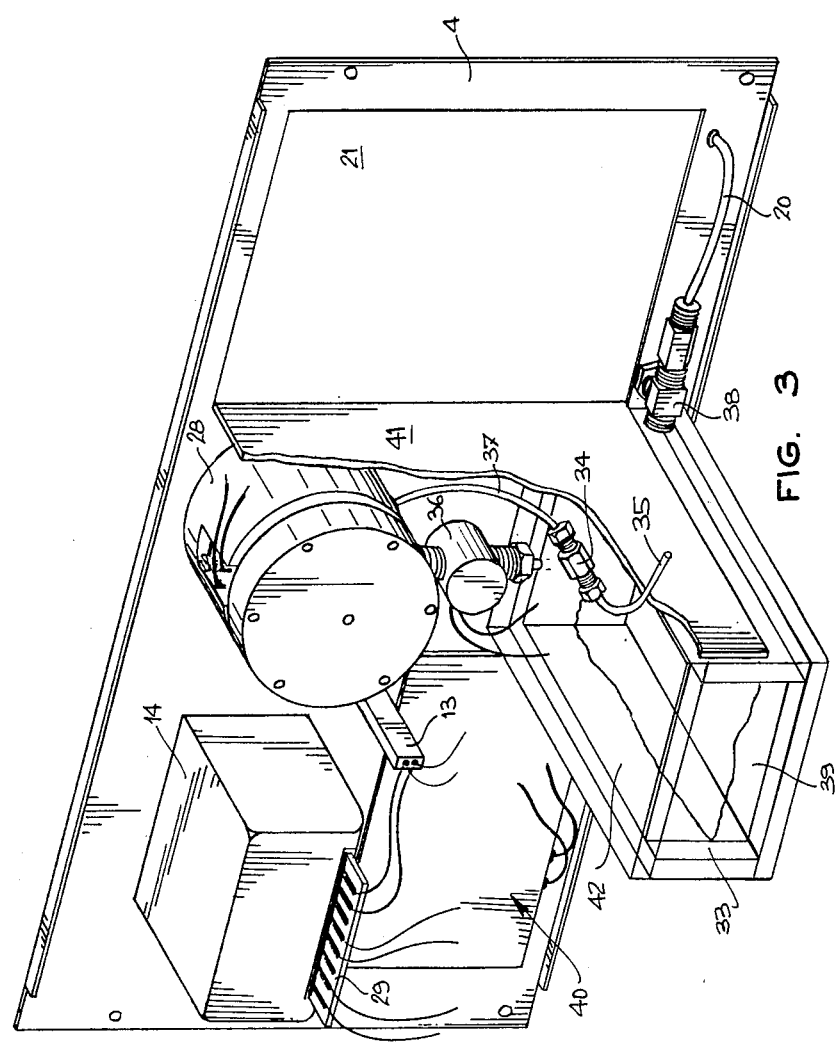
FIG. 3 is a rear view of the front panel of the measuring apparatus of FIG. 1.
Figure 4:
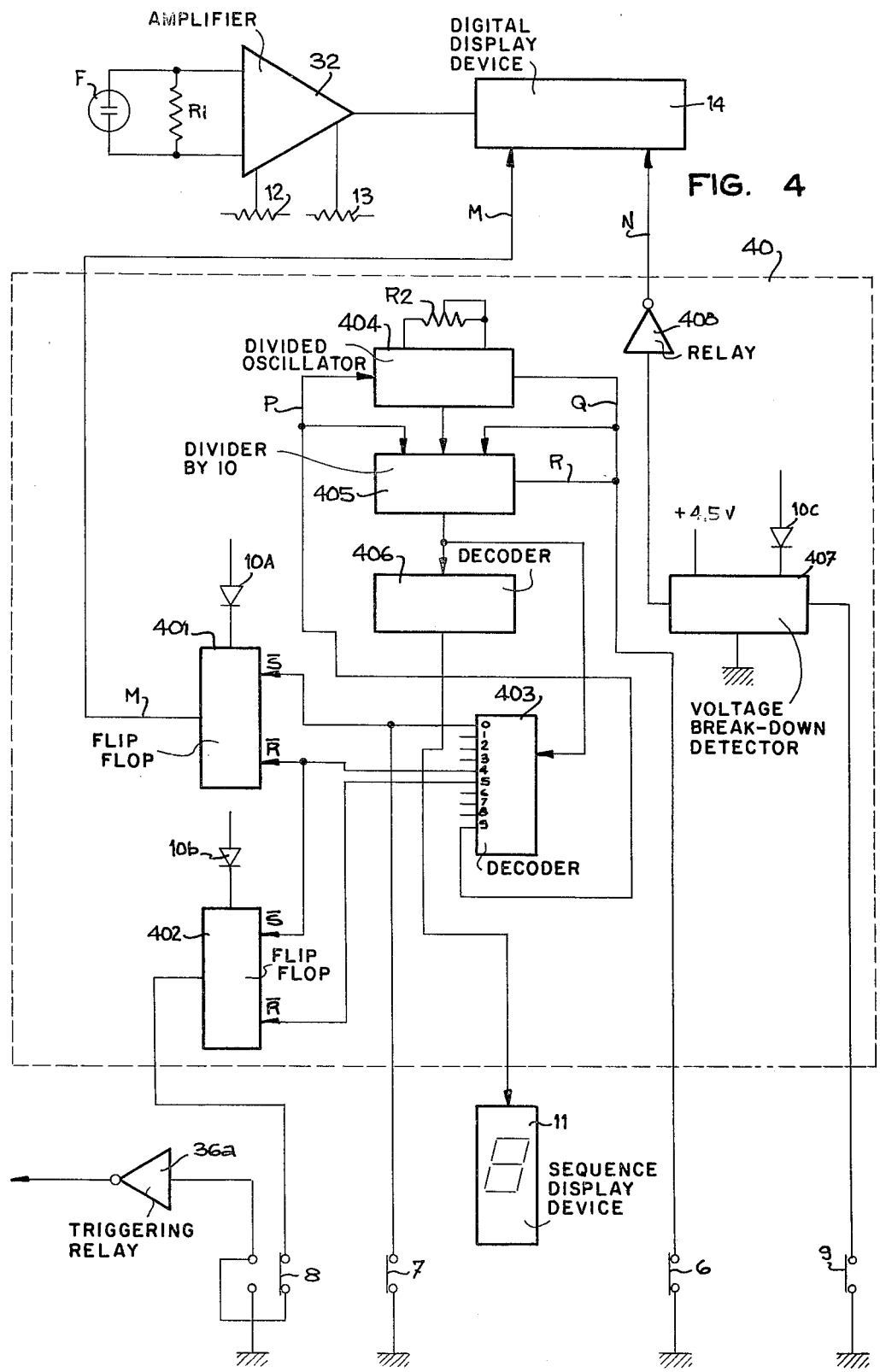
FIG. 4 is a schematic diagram of the electronic components used in the measuring apparatus of FIG. 1.

Referring generally to FIGS. 1, 2 and 3, the apparatus for measuring the concentration of hydrogen gas dissolved in a liquid substance comprises various electrochemical, electronic and mechanical devices incorporated in a housing 1 which is metallic, this eliminating effects of outside magnetic waves on the measure results. A handle 3 is firmly fixed on the top wall 2 of housing 1 and insulating supports 25 are provided on the external side of the casing floor 24. A removable panel 4, firmly attached to the housing by means of screws 5, holds a display device 14 displaying a direct reading in ppm of a measure signal representative of the concentration in hydrogen in the liquid substance under consideration, which signal is delivered by the electrochemical cell 28, the displayed concentration ranging from 0 to 19999 ppm. Under the display device 14, a potentiometric control button 13 is provided to calibrate the measure signal to allow a direct reading in ppm of the signal delivered by cell 28. That calibration button 13 is also connected to the amplifier 32 and to the display device 40 (FIG. 4). Close to the control button 13, there is provided a turn button 12 connected to a potentiometer for resetting to 0 the displayed values before each measurement.

The various operation settings of the measuring apparatus are carried on by means of four push-buttons 6, 7, 8 and 9, the three last of which are provided each with a light-emitting diode 10a to 10c, respectively. Button 6 is the start button which initiates automatically the apparatus measure cycle the sequence of which is displayed at 11 by a number varying from 0 to 9. Button 7 allows the setting of the display device 14 in a read mode while control button 8 allows to drain manually the liquid sample in the electrochemical cell 28, by operatively activating the electromagnetic valve 36. Button 9 furthermore operates, when the apparatus is started, to reset the values displayed on 11 and 14 as well as the measuring devices to their starting point, the light 10c associated with button 9 serving to indicate any breaking of the supply current to the apparatus during the measure proceedings.

A sample of the liquid of which the hydrogen content is to be determined is usually taken by means of a syringe (see FIG. 8A) and injected in one of the openings 15a or 15b of part 15 which is an integral part of the electrochemical cell 28, the air then contained in the cell being exhausted exteriorly through the other opening. Part 15 is made up of a transparent material, thereby allowing a direct view of the sample level injected in cell 28. After each measurement, the analyzed sample is drained either automatically, when a given number of time intervals of the operation sequence has elapsed, or manually by means of button 8, by triggering relay 36a of electrovalve 36. The used liquid 39 is then stored in a tank 33 provided with an hermetic cover 42 to avoid any splashing thereof during transportation of the apparatus. An elongated visual indicator 18, provided in the front panel 4, indicates the level of used liquid contained in tank 33. An air intake plug 17 is also provided for tank 33. When desired, that used liquid 39 is drained exteriorly by manually actuating lever 19 which opens valve 38 connecting the tank 33 to the tube 20.

Additionally, in order to obtain an accurate reading from the display device 14 about the hydrogen content of the liquid under consideration, a calibration of the apparatus is necessitated from time to time. That calibration is effected through the use of a liquid identical to that of the sample, which liquid contains a known concentration in hydrogen gas. Pursuant to an embodiment illustrated in FIGS. 1 to 3, that calibration liquid is housed in a cylindrical tank 22 firmly held in position inside the apparatus by means of a support 23 fixed to the floor 24 of the apparatus casing. A rectangular opening 21 effected in panel 4 provides easy accessability to the manually operated screw 27 which, when rotated clockwise, serves to inject a determined quantity of the calibration liquid into the measure chamber of the electrochemical cell 28 through tubes 35 and 37 connected to the return valve 34, the latter isolating tank 22 from cell 28. That valve 34 is maintained fixed on the metallic wall 41 orthogonally mounted on the front panel 4. The wall 41 is made from the folded part of opening 21 provided in the front panel and additionally functions to immunize the electrochemical cell 28 against the outside magnetic field effects.

The electronic part of the measuring apparatus is schematically illustrated in FIGS. 2 and 4, the latter showing in the form of a block diagram the electronic components of the system. A power supply unit 30 converts the AC voltage from the main, usually of 110 or 220 volts AC, through the three-wire thread 31 into DC voltages of 0, +5 and ±15 volts that are required for the operation of the various electronic measure and display devices. The signal generated by the electrochemical cell 28 is essentially a current having an intensity proportional to the hydrogen content of the liquid sample, wherefrom the illustration of the electrochemical cell has a current source F at FIG. 4. That current signal induces a voltage drop across the terminals of the load resistor R1, which feeds an amplifying device 32 the sensitivity and gain of which are respectively adjustable by means of the variable resistors 12 and 13, the amplifier gain being of approximately 1,000. As illustrated in FIG. 2 the amplifier 32 is mounted close to the electrochemical cell 28 on a support 42, the latter being firmly attached to plate 41 by fixing element 43. Such positioning of the amplifying device 32 near cell 28 contributes to reduce the background noise to a level lower than 1 microvolt calculated at the input of the amplifying device 32. On the other hand, the location of resistor R1 close to the amplifying device also allows a substantial reduction in the background noise and therefore an increase in the accuracy of the displayed measure. In the present case, the noise level of the apparatus is approximately of 1 ppm, resulting in a sensitivity of about 10 ppm and a reproducibility for successive analysis of a sample with a fixed concentration in hydrogen gas in the order of 1%.

The amplified signal directly supplies the digital display device 14 through its terminal board 29 (FIG. 3). The display device advocated here is of the type available from Datel Corp., Mass. U.S.A., under catalogue No. 4100 L; any equivalent type could of course be used. A control circuit 40 mounted on a printed circuit board and in parallel with the removable panel 4 governs automatically the operating time of relay 36a which actuates the electrovalve 36 to drain the sample from the cell, controls the time intervals of the operation sequence of the apparatus, displayed in 11, and determines the instant of setting the displayed value into memory. That control circuit 40 is essentially constituted of a base clock which generates the sequence of 10 regular intervals varying from 0 to 9, each interval being of about 2 minutes and being adjustable at will by means of the variable resistor R2. It is those various states of the sequence which are displayed in 11 and which indicate a definite step in the measure and operation process of the apparatus. In addition, each time interval of the sequence remains constant once adjusted.

In the embodiment of the control circuit 40 illustrated in FIG. 4, the divider-oscillator 404 generates a signal corresponding to the unitary duration of the operation sequence of the apparatus and which is adjusted by the variable resistor R2. This oscillator feeds a divider by 10, 405, which defines the 10 states (from 0 to 9) of the sequence. The output of divider 405 feeds both decoders 403 and 406. Decoder 406 of the BCD type triggers the segments of the display device 11, which are 7 in number, whereas decoder 403, of the digital type, defines the automatic operation instants of the display device 14 through the flip-flop 401, and of relay 36a which triggers the electrovalve 36 according to the state of flip-flop 402. The device 407 constitutes a detector that insures the resetting at 9 of the display 11 by acting on divider 406 and which, additionally, controls the feeding of display 14 through relay 408 in the event of a voltage breakdown of the system, thereby avoiding any display of erroneous measures. The display device 14 may be reactivated by pressing the 0 resetting button 9 connected to the voltage breakdown detector 407.

At starting, the oscillator-divider 404 is blocked, its input P being activated. By pressing the start button 6 connected to the input Q of the oscillator 404, the input P is then deactivated, thereby unblocking the oscillator which then starts operation. For the same reasons, the inputs P and Q also feed the divider 405; the measurement sequence is thus started and the states of that sequence are displayed in 11. It is to be noted that when the input P is not energized, e.g. when the sequence is on, the input Q is not operative, this insuring a start at 0 of the system in all cases and eliminates any start attempt when the sequence is on. Initially, at state 0 of the sequence, decoder 403 energizes the input S of the flip-flop 401 to block the display in device 14 of the measure signal supplied by the amplifier 32 by a signal delivered through the output M of the flip-flop 41, when the system is on the automatic mode. At time 4 of the sequence, decoder 403 reverses the state of the flip-flop 401 to allow the display and the setting into memory in 14 of the signal from the amplifier 32 at that time. At that same interval 4, the decoder 403 changes the state of the flip-flop 402 through its input S by actuating the relay 36a of the electrovalve 36 when the push-button 8 is is the position shown. At time 5, the decoder 403 applies a signal to the input R of the flip-flop 402 which then returns to its initial state, thus ending the draining step of the liquid contained in the electrochemical cell 28. Finally, at state 9 of the decoder 403, the input P of the oscillator 404 and of divider 405 is energized thereby terminating the measure sequence, at this time the display 11 indicating 9.

As mentioned above, button 7 permits a continuous display in 14 of a signal delivered by the amplifier 32 through the grounding of the input S of the flip-flop 401 whereas button 8, when actuated, permits the drain of the liquid contained in the electrochemical cell 28 at any time during the sequence.

Figure 5:
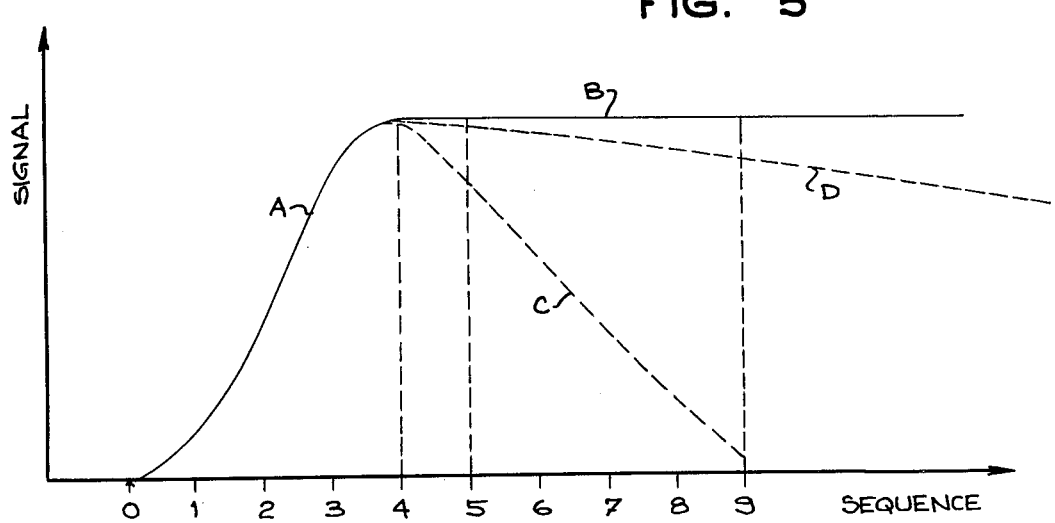
FIG. 5 illustrates the operation sequence of the measuring apparatus of FIG. 1.
Figure 7:
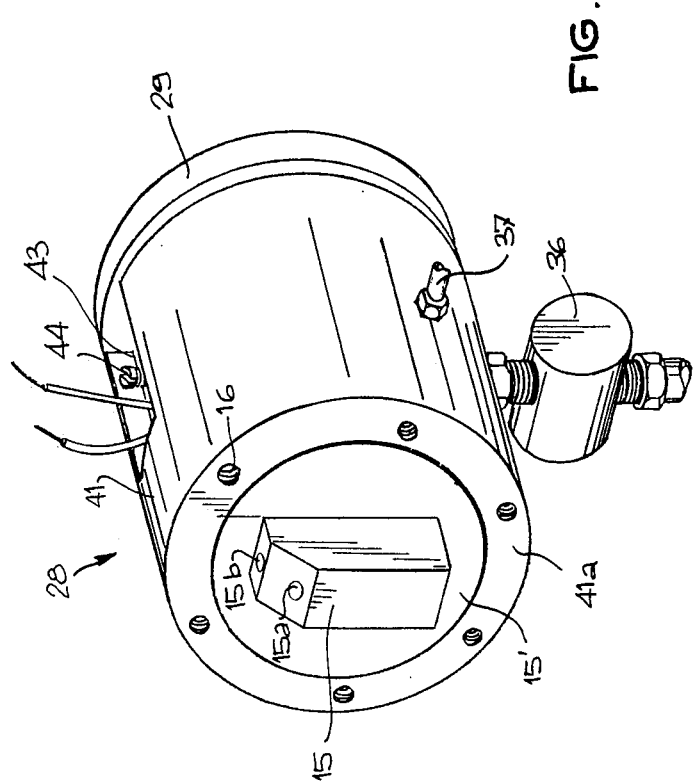
FIG. 7 illustrates the electrochemical cell with the various parts assembled, used in the apparatus of FIG. 1.

FIG. 5 shows the various time intervals of the sequence vs the displayed signal according to the operating mode of the apparatus which is as follows. When the apparatus is started, the light indicator 10c is turned on to indicate that the apparatus is normally supplied, but no value is displayed by the display device 14. The zero-setting button 9 is then pressed and immediately after the read button 7 is pushed to energize the corresponding light indicator 10a and to display in 14 the signal value of the cell. The apparatus stabilizes itself for a predetermined period, from 15 to 30 minutes, at least until the signal displayed in 14 is stabilized. Then, the value displayed in 14 is then set to 0 by means of the potentiometer 12; the apparatus is now ready for the the taking of a first measurement.

At this stage, prior to the measurement of an unknown hydrogen concentration of a sample, it may be advisable to calibrate the electrochemical cell 28. For that purpose, the handle 27 of cylinder 22 is rotated to inject some calibration liquid into the sample chamber of the electrochemical cell 28 and in a quantity sufficient to fill completely that chamber as can be seen through the transparent member 15. The measurement sequence is then started by actuating the push-button 6. At this time which corresponds to the state 0 of the sequence, the value displayed in 14 is nul, but the signal almost immediately starts increasing. The signal increases following the exponential curve A during the time intervals 0, 1, 2 and 3, displayed in 11, and, near the end of the time interval 3, the calibration potentiometer 13 is manipulated so that the value displayed in 14 corresponds to the already known value of the hydrogen concentration in the calibration mixture.

At instant 4, the value then displayed (curve B) is set into memory in the display device 14 and the electrovalve 36 is activated to drain the liquid contained in the electrochemical cell 28 into the tank 33. During the whole interval 4, the light indicator 10b remains on to indicate that the draining of the measured liquid is normally effected.

At interval 5, the electrovalve 36 is deenergized and the signal from the electrochemical cell 28 then decreases continuously (curve C) until it reaches a value close to 0 when the sequence displayed in 11 indicates 9. The decreasing of the signal may be visualized on the display apparatus 14 by pressing on the read mode push-button 7. It is to be noted that the start push-button 6 becomes operative only when the sequence indicates 9. In all cases, the electrovalve 36 may be manually actuated to drain the cell by means of the push-button 8.

Curve D of FIG. 5 shows the behavior of the signal displayed in 14 when the sample liquid is not drained at instant 4. It is noted that the signal supplied by the electrochemical cell 28 is actually at a maximum value at the end of the interval 3.

When needed, after the resetting to 0 of the apparatus through potentiometer 12, it is of course possible to proceed to a second injection of the sample liquid into the electrochemical cell, this being performed in order to ascertain the reproducibility of the system and to complete the fine adjustements relative to the measurement procedure. In this case, the steps described above are then simply resumed again.

Pursuant to the calibration, the analysis of the liquid sample containing an unknown concentration in hydrogen, is undertaken. That sample is injected by means of a syringe or any other adequate means into the measure chamber of the electrochemical cell 28 through the opening 15a of the transparent part 15. The measuring procedure is then started and the above-discussed operation mode of the apparatus is followed. The apparatus having been previously calibrated, the value of the hydrogen concentration in the liquid may then be read directly in ppm at step 4 of the measure sequence.

It is to be noted that it is not necessary to calibrate the apparatus before each measurement. Indeed, a weekly or even a monthly, calibration is largely sufficient, and mainly depends on the frequency of use of the apparatus.

Figure 6:
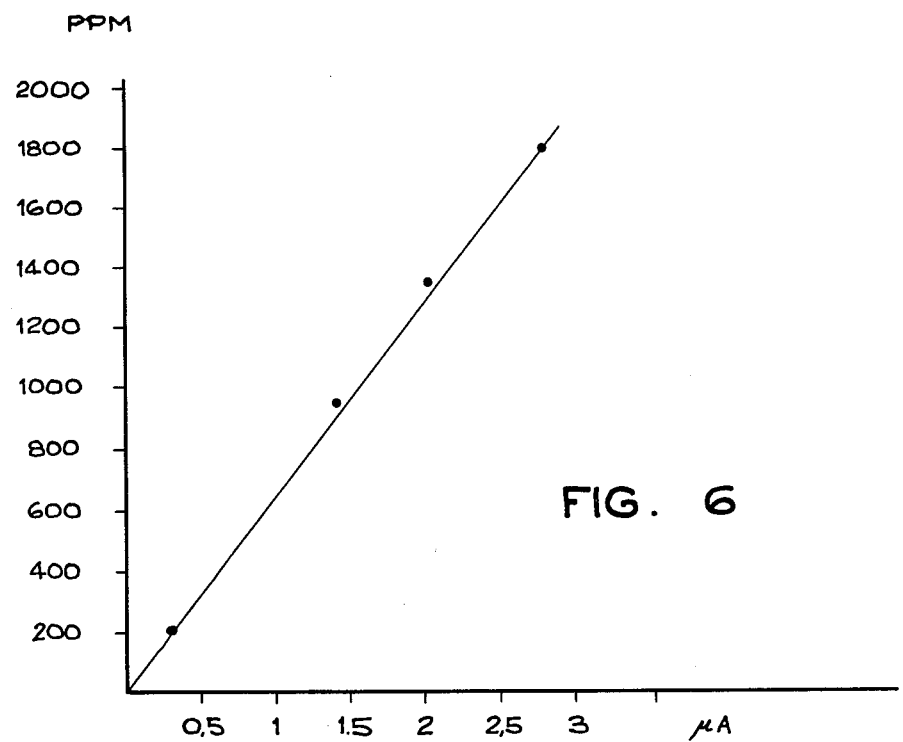
FIG. 6 is a graph illustrating the linearity of the displayed signal in function of the concentration of hydrogen in a liquid.

FIG. 6 gives a graph of the results obtained by a measuring apparatus identical to that described above. That graph illustrates well the linearity of the displayed signal in function of the hydrogen content of the liquid sample for various concentrations. Such linearity of the curve ascertains the outstanding reproducibility and great reliability of the measuring apparatus in connection with the displayed results.

FIGS. 7, 8A, 8B and 9 show an arrangement of the electrochemical cell 28 for detecting and measuring the concentration of gaseous hydrogen in a liquid sample S. Liquid sample S (FIG. 8A) is injected into the opening 15a of the transparent part 15 by means of a syringe T the extremity of which is snuggly adapted to the widening 15a. By pressing the piston of syringe T, the sample S is injected into the channel 15c to fill the measure chamber 58 of the cell 28, that chamber having a capacity of about 3 cc; the air previously contained in the chamber 58 is then exhausted exteriorly through conduit 15d which communicates with the winding opening 15b.

The transparent part 15 is provided with a circular base 15' which is set on the surface 41b of the support part 41 to form therewith a mortise-tenon type joint, the thickness of base 15' being substantially equal to the depth of flange 41a provided in part 41. When assembling the transparent part 15 onto the surface 41b, the conduits 15c and 15d are placed in registry with the openings 15'c and 15'd, respectively, pierced in that surface 41b. On the other hand, the ring joints 15e (FIG. 8A) housed in grooves formed in the transparent part 15 insure a tight joint between the channels 15c and 15d and the openings 15'c and 15'd, respectively.

The liquid sample S contained in the chamber 58 is in contact with a polymeric membrane 45 which extends across chamber 58 while resting against the backpart of the ring-shaped flange 41d formed inside the cylinder 41. Polymeric membrane 45 allows diffusion of the hydrogen gas contained in the sample towards the detecting unit of cell 28. To avoid all intrusion of the sample S inside the detecting unit, a ring joint 41e is provided between the polymeric membrane 45 and the flange 41d. When assembled, membrane 45 is firmly maintained in position through compression between the wide flange 46a of part 46, which houses the detecting unit, and the flange 41d of the outmost part 41. On the other hand, the main parts constituting the detecting device are, besides the polymeric membrane 45 permeable to the hydrogen gas, a detection electrode 49 at which occurs the oxydation of the hydrogen diffusing through the pores of that polymeric membrane 45, an electrode 51 in contact with an oxygen-containing gas, such as air, and at which occurs the reduction of the oxygen of that gas, and an electrolyte E in contact with both electrodes 49 and 51, that electrolyte being selected so as to carry out the oxydo-reduction reactions at the two electrodes.

The function of the polymeric membrane 45 is to allow the hydrogen gas to diffuse inside the detecting unit, as mentioned above, but also to prevent the sample S from contaminating the electrode 49, particularly when the sample S is an oleaginous liquid. Among known materials, it has been found that polyethylene and polytetrafluoroethylene or Teflon (a trademark) are acceptable to make up the polymeric membrane 45 since the pores of those materials have such a size as to permit a preferential diffusion of the hydrogen gas therethrough. It is to be noted that the diffusion rate of hydrogen is directly related to the thickness of the membrane 45, therefore the thinner and membrane 45, the more quickly the oxydation reaction will be detected.

On the other hand, the electrodes 49 and 51 are porous and respectively permeable to hydrogen and oxygen. An adequate type of electrodes used is constituted of platinum black bound with polytetrafluoroethylene, supported by a metallic grill made up of either platinum or tantalum coated with a layer of gold. By way of example, an arrangement and a process for making that type of electrodes is described by L. W. Niedrach and H. R. Alford in "The Journal of the Electrochemical Society", volume 112, p. 117 (1965). In respect of the electrolyte E used, the latter is to be of such a composition so as to enable the occurrence of the reaction of electrochemical oxydation of the hydrogen at electrode 49 and that of reduction of oxygen at electrode 51. For that purpose, any type of electrolyte respecting the electrochemical operation principle of the detector in accordance with the present invention may be used. Thus the oxydo-reduction reaction can be initiated by means of an electrolyte constituted by an acid, such as phosphoric, sulfuric or perchloric acids, by an alkali solution such as the potassium or sodium oxides, or even a solid electrolyte formed with an ion exchanging membrane.

From the above description, the detection of the hydrogen content is permitted to be performed in a continuous way through the electrochemical cell, since the hydrogen gas contained in the sample S steadily diffuses through the polymeric membrane 45 and is readily oxydated through the electrochemical reaction by means of the electrolyte E at the detection electrode 49. Similarly, there occurs the reaction of reduction of the oxygen gas present in the reference gas, at the electrode 51 also in contact with the electrolyte E. As a result, the oxydation of hydrogen creates an electronic current, each hydrogen molecule freeing two electrons during the reaction process, and the intensity of that current creates a potential drop across resistor R1 (FIG. 4), which drop is displayed in 14 after being amplified. The current observed at the output of the detecting unit is then proportional to the concentration of the hydrogen gas dissolved in the sample S, and is in accordance with the following formula:

$$i = (nFDSc/d)$$

where
- "i" is the current observed,
- "n" is the number of electrons involved in the reaction, that is two in the present case,
- "F" is the Faraday constant which equals 96,490 Coulomb/equivalent,
- "D" is the diffusion coefficient of the polymeric membrane used,
- "S" is the membrane area in contact with the sample,
- "c" is the hydrogen concentration in the sample,
- "d" is the thickness of the membrane.

Figure 8B:
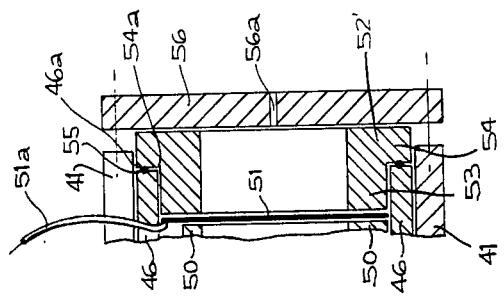
FIGS. 8A and 8B are cross-sectional views of the electrochemical cell of FIG. 7.
Figure 8A:
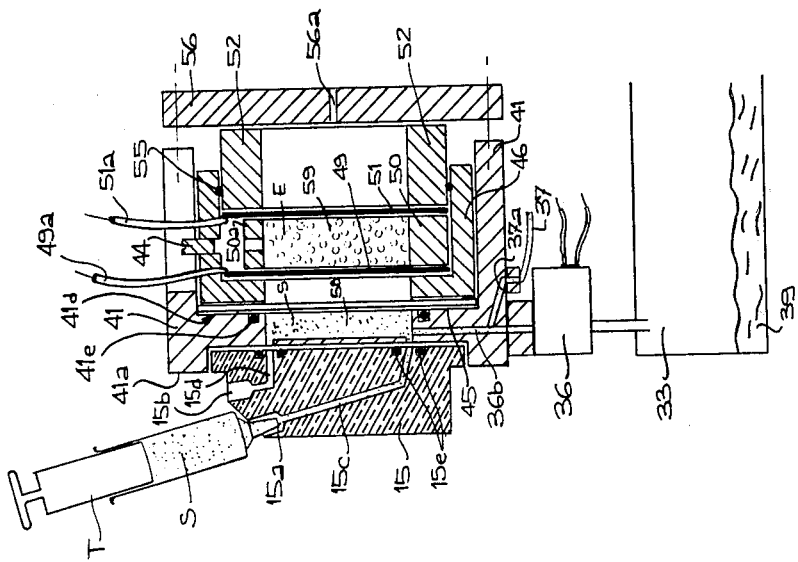
Figure 9:
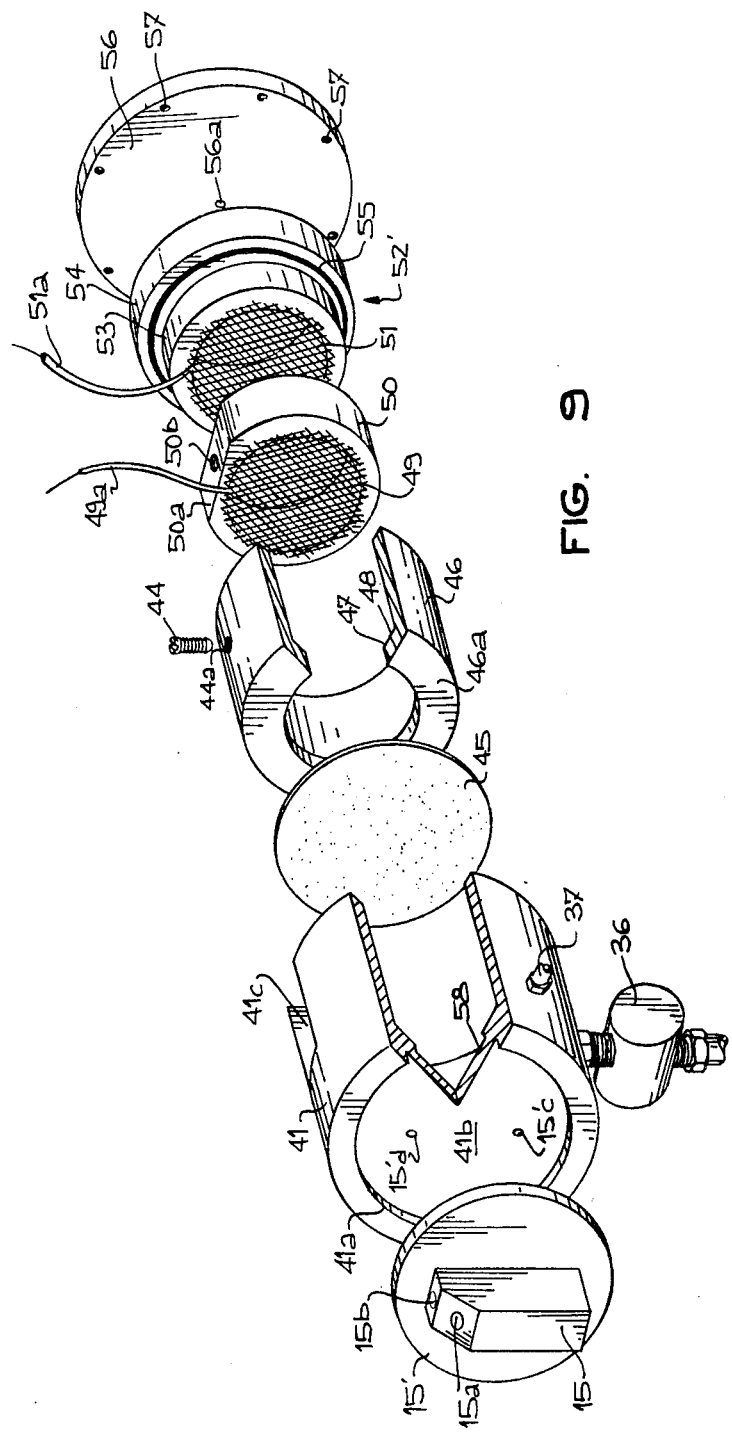
FIG. 9 is an exploded view of the electrochemical cell of FIG. 7 incorporating the embodiment illustrated in FIG. 8B.

As illustrated in FIG. 8A, a variant of which is shown in FIG. 8B which is part of the exploded view of FIG. 9, the porous electrodes 49 and 51 are firmly set into position by compression between the holding parts 46 and 52 and part 50 containing the electrolyte A. In addition, the dimension of those cylindrical parts is such as to allow a snuggly and tight encasing of one into another. It is also to be noted that the tightness between part 46 and 52 is ascertained through the use of a ring joint 55 which, in the case of FIG. 8A, is provided between the external surface of part 52 and the internal surface of part 46. A variant of the arrangement of part 52 is illustrated in FIG. 8B and designated by 52'. In FIG. 8B, part 52' comprises an elbow 54 the surface 54a of which rests against the shoulder 46a of part 46 and between which the tightness ring joint 55 is housed. The latter arrangement permits a less strict tolerance in the machining of part 52' than of part 52 of FIG. 8A, while achieving an excellent tightness hermetic joint parts 46 and 52'.

Once assembled, parts 46, 50, 52 or 52' are firmly maintained into their respective position by the external holding member 56 which is securely attached to part 41 by screws or any other fixing means running through the holes 57. That mounting and tightening method offers the advantage of avoiding any radial or lateral movement of parts 46, 50 and 52. Indeed, parts 41 and 56 being in steel or in brass while parts 46, 50 and 52 or 52' are in polypropylene or any other chemically inert material, the tightening of part 56 onto part 41 results in slightly deforming through compression parts 46, 50 and 52 or 52' one on another so as to provide a suitable way of maintaining together the various parts of the detecting unit in their respective position and for avoiding any leakage of electrolyte E. Moreover, in part 56, a central opening 56a serves as air inlet to the electrode 51.

In addition, in the lower part of member 41, a channel 36b links chamber 58 to the electrovalve 36 to drain the liquid sample into the tank 33 when interval 4 of the operation mode described above is reached. That channel 36b also communicates with a second channel 37a which is connected to tube 37 through which is injected the calibration liquid provided from cylinder 22 (FIG. 2) towards the inside of chamber 58 of the cell.

Moreover, a threaded hole 44a is provided in the lower part of member 46, which hole is set in registry with the opening 50b formed on the truncated surface of part 50, to allow the filling of the lowest part of the cylindrical part 50 in electrolyte E. A plug 44 closes the opening 44a when the filling is completed. In addition, a rectangular opening 41c made in part 41 permits access to the opening 44a as well as the outlet of wires 49a and 51a respectively connected to electrodes 49 and 51.

Figure 10:
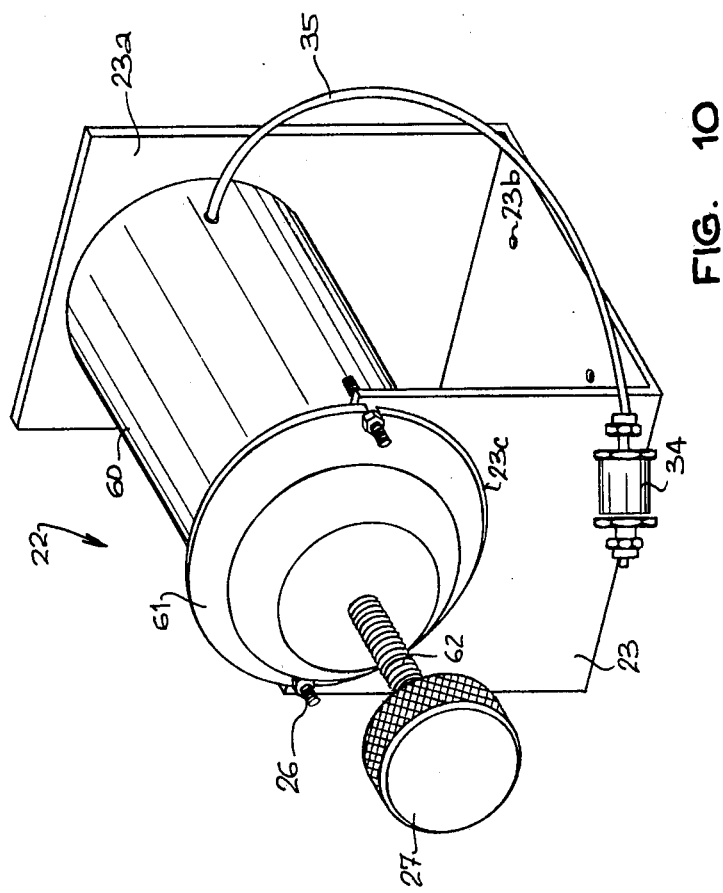
FIG. 10 shows the calibration device mounted on a support, this device being used together with the apparatus of FIG. 1.
Figure 11:
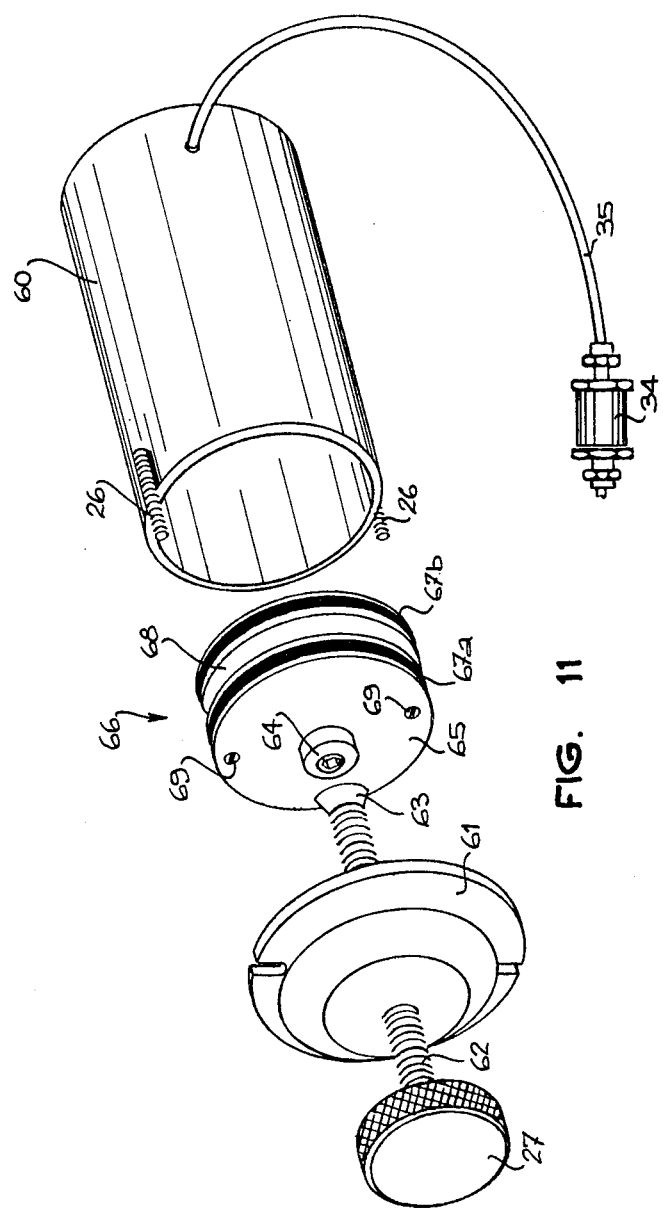
FIG. 11 is an exploded view of the calibration apparatus of FIG. 9.
Figure 12:
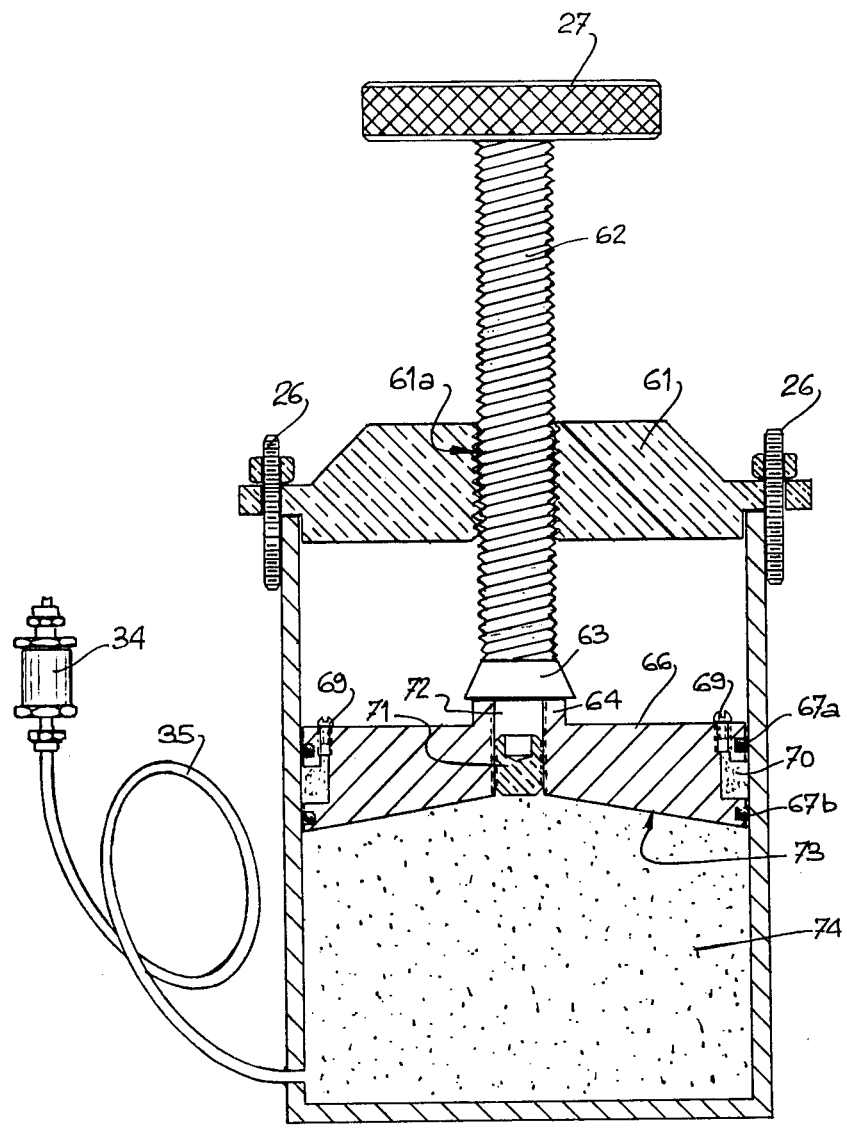
FIG. 12 is a cross-sectional view of the parts of the calibration apparatus of FIG. 9, as assembled.

FIGS. 10, 11 and 12 illustrate in detail an embodiment of the calibration device 22 shown in FIGS. 1 and 2.

That calibration device generally comprises a cylindrical metallic casing 60 having one extremity open and onto which is set the metallic cover 61 which is provided with a threaded central opening through which a screw 62 is displaced when exteriorly moved in rotation by means of knob 27. The cover is tightly maintained against the opening of cylinder 60 by means of any suitable fixing means, such as the set of screws and nuts as illustrated. The internal wall of cylinder 60 is worked smooth so as to allow the free displacement of piston 66 which, when moved axially towards the bottom of the cylinder, compresses the calibration liquid 74 containing a known concentration of hydrogen to eject same through tube 35 and the non-return valve 34 towards the electrochemical cell 28 described above. The free end of screw 62 includes an abutment 63 which leans on the protuberance 64 centrally disposed on the external face of piston 66, to move the latter along the longitudinal axis of the cylinder 60. That protuberance 64 is provided with a central threaded opening 72 for the filling of the cylinder with the calibration liquid; upon completion of the filling, a cap 71 is screwed in the opening 72. The internal surface 73 of piston 66 is made angular so as to exhaust completely the air present inside the cylinder at the filling time.

Moreover, the tightness of the calibration device is ascertained by means of two sealing joints 67a and 67b, these being concentrically mounted around the periphery of piston 66, and by means of a mercury film 70 disposed in a circumferential groove and between the sealing joints 67a and 67b, that mercury film preventing in a highly efficient manner the hydrogen gas in the calibration liquid from diffusing outside the container, on the one hand, and allowing the piston to slide smoothly along the internal wall of the cylinder 60, on the other hand.

Replenishment of the cylinder 60 with calibration liquid may be performed according to the following proceedings. The ring joints 67a and 67b of piston 66 are first covered with grease and then set into position in their respective grooves. Piston 66 is inserted in the cylinder 60 which is thereafter filled up with the calibration liquid having a known-hydrogen gas content. At this stage, it is to be ascertained that the cylinder is actually fulfilled and that no air bubbles have been confined therein. Plug 71 is then secured while ascertaining that there is a slight excess in calibration liquid. Thereafter, the two plugs 69 of the mercury tank 70 are removed and the latter is filled up, following which the two plugs are set back into place. Finally, cover 61 is secured to the cylinder 60 while taking care of setting the extremity 63 of screw 62 well in abutment with element 64 of piston 66. The above steps completed, it is desirable to let the calibration device at standstill for a few days so that the hydrogen gas and the liquid in which it is dissolved may reach a stable equilibrium. It is to be noted that the quantity of calibration liquid contained in the device is of approximately 200 to 250 cc, which allows to perform about 75 calibrations of the electrochemical cell.

When mounted in the measuring apparatus (see FIGS. 1, 2 and 10), the calibration device rests horizontally onto a support 23 which is U-shaped and the front part of which has been cut off in a semi-circular configuration 23c wherein snuggly fits the cylinder 60. The rear part of cylinder 60 is inserted in an opening provided in leg 23a whereas the support 23 is firmly secured to the bottom of the measuring apparatus casing by means of screws running through the holes 23b.

Figure 13:
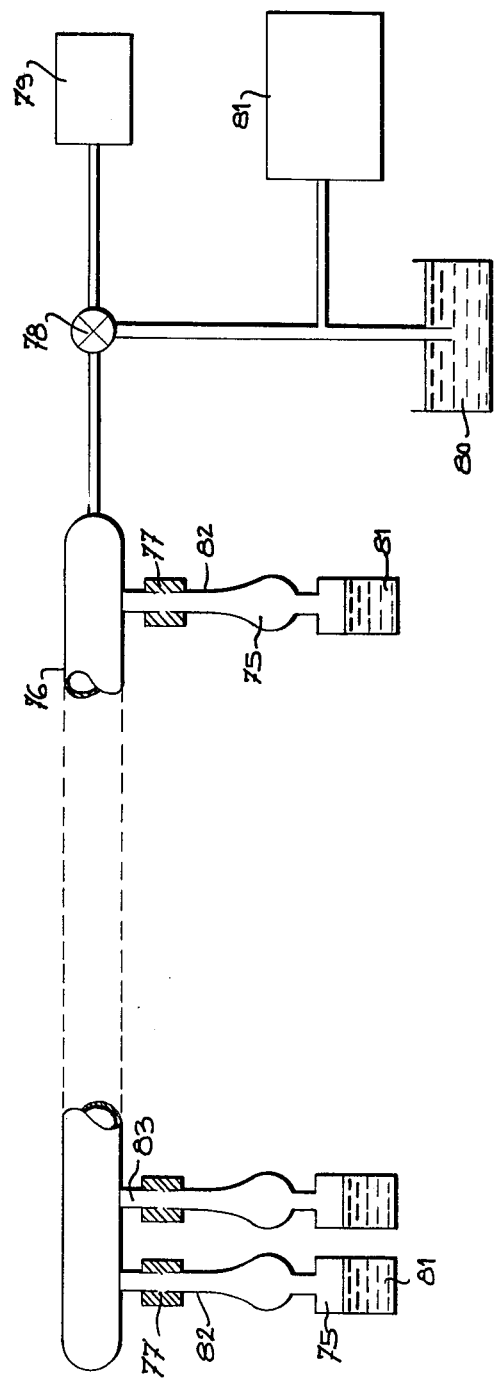
FIG. 13 illustrates a system for preparing glass ampullas containing a calibration liquid.

Following a further embodiment, it is proposed to utilize individual constant volume glass ampullas, for instance of a 10 cc capacity, for the calibration of the electrochemical cell, each ampulla containing about 5 cc of calibration liquid. The system illustrated in FIG. 13 and its operation mode permit the preparation of a few dozen ampullas at once. The system is generally constituted of an elongated glass tube 76 provided with a series of conduits 83 disposed along the longitudinal wall of the tube, each conduit communicating with one ampulla 75. One extremity of the glass tube 76 is connected to a three-way valve 78 which is in turn connected to a vacuum pump 79 and to a tank 81 containing a nitrogen-hydrogen mixture in a proportion of about 1 to 3% vol./vol. The conduit connecting valve 78 to tank 81 also leads to a reservoir 80 containing water and acting as a pressure indicator. Besides, rubber bands 77 sealingly connect ampullas 81 to conduits 83 of tube 76.

Once the ampullas have been connected to conduits 83, the degasifying of the liquid 81 in each ampulla is effected by activating the vacuum pump 79 for about a few hours. Then, the conduits connecting valve 78 to tank 81 are cleared out through a bubbling of the gaseous mixture for a few minutes, and thereafter, valve 78 is manipulated so as to fulfill tube 76 and ampullas 75 with the gaseous mixture, the latter step being performed under atmospheric pressure. Finally, the ampullas are successively sealed at their neck area 82 and stored for a few weeks. After that storing period, one or more ampullas from the same batch are analyzed in order to determine their hydrogen content. For that purpose, the ampulla is scratched with a file at the neck level and then broken through a lateral pressure with the thumb. The hydrogen gas concentration thus determined is indicated on the other ampullas prepared under the same conditions. That calibration method has provided excellent results in terms of accuracy and stability in the calibration procedure and consequently may be widely used, particularly when a more compact and light weight measuring apparatus is desired. It is to be noted that, when using that calibration method with ampullas, the input conduit 37 (FIG. 9) connecting the measure chamber 58 of the electrochemical cell to the calibration cylinder 22, must then be blocked.

It is to be understood that modifications may be brought to the measuring apparatus described above without hampering the gist of the present invention. Indeed, it is deemed to be within the skill of any able technician to replace the convertor 30 (FIG. 2) by a direct current source provided with a voltage regulator to feed the various electronic devices of the instant measuring apparatus. Similarly, it is technically feasible to substitute to the digital display device 14 either an equivalent analog device or a peak signal detector or even more a graph recording device. Consequently, the scope of the present invention is limited only by that of the claims which follow.

We claim:

1. An apparatus for measuring the concentration of gaseous hydrogen dissolved in a liquid substance, comprising:

an electrochemical detection device for determining said concentration of hydrogen in said liquid substance, and generating a current having a value proportional to said concentration; said detection device comprises: first and second electrodes; an electrolyte means, separating said electrodes for causing a reaction of oxidation of the hydrogen diffused through a polymeric membrane at said first electrode, and a reaction of reduction of an oxygen-containing gas at said second electrode so as to generate said current proportional to the concentration of gaseous hydrogen; and a polymeric membrane permeable to hydrogen, separating said liquid substance from said first electrode;

a device connected to said detection device to drain therefrom said liquid substance;

a display device for displaying the concentration detected by said detection device;

a circuit for amplifying a voltage corresponding to said current proportional to said concentration when said current flows through a load resistance mounted across the input of said amplifying circuit;

potentiometers acting on the amplifying circuit for controlling calibration and zero-setting of said display device; and a control circuit for governing the operation sequence of said detection device, said drain device and said display device in accordance with a predetermined operating sequence, said control circuit comprising an oscillator-divider generating a signal corresponding to an adjustable unit time interval of said predetermined operation sequence; a divider receiving said unit time interval signal and feeding a first decoder, said first decoder energizing a display unit displaying a state of said predetermined sequence, and feeding a second decoder defining actuation instants of said drain device and said display device, said second decoder controlling, according to the state of the sequence defined by said divider, the time of setting into memory in said display device of a measure supplied by said detection device, and the time of starting and stopping said drain device said second decoder also generates a signal for blocking said oscillator-divider when said predetermined sequence is terminated.

2. An apparatus as claimed in claim 1, comprising means for calibrating said measuring apparatus through injection into said detection device of a sample liquid substance identical to said liquid substance to be measured except that said sample has a known content of gaseous hydrogen.

3. An apparatus as claimed in claim 2, characterized in that said calibration means comprise ampullas each containing said liquid identical to said liquid substance to be measured and having a known concentration in gaseous hydrogen.

4. An apparatus as claimed in claim 1, wherein said detection device comprises a cylindrical housing having an open extremity and another extremity closed by a wall so-shaped as to form with said polymeric membrane a chamber for retaining said liquid substance; a first cylindrical holding member coaxially mounted within said housing; a generally cylindrically shaped member to contain said electrolyte and mounted within said first holding member; a second holding member, also cylindrical, resting against said electrolyte containing member and lying partially inside said first holding member; and a cylindrical fixing member secured to said housing for firmly maintaining into position said polymeric membrane between the housing and the first holding member, said first electrode being located between the first holding member and the electrolyte containing member, and said second electrode being located between the electrolyte containing member and the second holding member.

5. An apparatus as claimed in claim 4, wherein seal joints are provided between the first holding member and the cylindrical housing as well as between the first and second holding members so as to prevent the liquid substance from contacting said first electrode and said electrolyte from exhausting outside of said detection device.

6. An apparatus as claimed in claim 5, wherein a conduit connects the lower part of the liquid substance retaining chamber to said drain device.

7. An apparatus as claimed in claim 5, wherein a transparent part externally rests against said wall of the cylindrical housing and comprises conduits mounted in registry with holes provided in said wall for injecting said liquid substance into said retaining chamber.

8. An apparatus as claimed in claim 1, wherein said divider is a divider by ten which defines ten equal time interval states of said predetermined sequence.

9. An apparatus as claimed in claim 8, characterized in that said display unit is digital and is constituted of segments which are energized by said first decoder according to the state of said sequence defined by said divider.

10. An apparatus as claimed in claim 1, 8 or 9, characterized in that said control circuit further comprises a voltage breakdown detector acting on said divider and on said display device and a zero-setting means for reenergizing said voltage breakdown detector.

11. An apparatus as claimed in claim 1, wherein means are provided for manually actuating said display device and said drain device at any time during said predetermined sequence.

12. An apparatus as claimed in claim 1, wherein, said calibration means includes a cylindrical casing having an open extremity and onto which is secured a removable cover, and means for compressing the calibration liquid in said casing towards said detection device through a non-return valve.

13. An apparatus as claimed in claim 12 wherein said compression means comprise a piston snuggly fitting inside said cylindrical casing, the piston including two peripheral seal joints, concentrically mounted, and between which is provided a circumferential groove lodging a mercury film, the two seal joints and the mercury film being in contact with the internal wall of said cylindrical casing so as to prevent the hydrogen in said calibration liquid from diffusing exteriorly of the casing.

14. An apparatus as claimed in claim 12, characterized in that a screw provided with a handle extends through a threaded opening made in the center of said cover and rests in abutment against the center of said piston to move the latter in compression in order to eject the calibration liquid towards said detection device.

15. An apparatus as claimed in claim 1, wherein said drain device comprises an electrovalve for ejecting when energized, said liquid substance from said electrochemical cell.

16. An apparatus as claimed in claim 15, further comprising a used liquid retaining tank for receiving the liquid substance ejected by said electrovalve, and a manually operated valve mounted on said retaining tank for ejecting said used liquid from said tank.

* * * * *